United States Patent [19]

Schinazi et al.

[11] Patent Number: 5,159,067
[45] Date of Patent: Oct. 27, 1992

[54] 5'-DIPHOSPHOHEXOSE NUCLEOSIDE PHARMACEUTICAL COMPOSITIONS

[75] Inventors: Raymond F. Schinazi, Decatur, Ga.; Jean-Pierre Sommadossi, Vestavia, Ala.; Chum K. Chung, Athens, Ga.

[73] Assignees: University of Georgia Research Foundation Inc., Athens, Ga.; University of Alabama at Birmingham Research Foundation, Inc., Birmingham, Ala.

[21] Appl. No.: 377,617

[22] Filed: Jul. 10, 1989

Related U.S. Application Data

[63] Continuation-in-part of Ser. No. 104,438, Oct. 2, 1987, Pat. No. 4,916,122, which is a continuation-in-part of Ser. No. 7,473, Jan. 28, 1987, abandoned.

[51] Int. Cl.$^5$ .................. C07H 17/00; C07D 473/00; C07D 333/02; C07D 307/00
[52] U.S. Cl. ........................ 536/27; 536/28; 536/29; 544/269; 549/29; 549/430
[58] Field of Search ............... 514/47, 48, 51; 536/26-29; 544/269; 549/29, 430

[56] References Cited

U.S. PATENT DOCUMENTS

| | | | |
|---|---|---|---|
| 3,328,389 | 6/1967 | Shimizu et al. | 514/49 |
| 4,230,698 | 10/1980 | Bobek et al. | 514/49 |
| 4,604,382 | 8/1986 | Lin et al. | 514/49 |
| 4,847,244 | 7/1989 | Rideout et al. | 514/50 |
| 4,879,277 | 11/1989 | Mitsuya et al. | 514/49 |
| 4,916,122 | 4/1990 | Chu et al. | 514/49 |

FOREIGN PATENT DOCUMENTS

| | | |
|---|---|---|
| 0352248 | 2/1990 | European Pat. Off. . |
| 0357571 | 3/1990 | European Pat. Off. . |
| 2042290 | 2/1971 | France . |
| 2051064 | 4/1971 | France . |

OTHER PUBLICATIONS

Alarcon, et al., *Antimicrobial Agents and Chemotherapy* vol. 32, No. 8, Aug. 1988, pp. 1257-1261.
Roseman et al., *Journal of the American Chemical Society*, vol. 83, Feb. 1961, pp. 659-663.
McDowell et al., *Chemical Abstracts*, vol. 104, No. 1, Jan. 1986, p. 23.
Pazur, John D., *Chemical Abstracts*, vol. 90, No. 24, Jun. 11, 1979, p. 315.
Keppler, et al., *Metabolic Compartmentation*, 1982, pp. 147-203.
Datema, et al., *Pharmac. Ther.*, vol. 33, 1987, pp. 221-286.
Alcina, et al., *Antimicrobial Agents and Chemotherapy*, vol. 32, No. 9, Sep. 1988, pp. 1412-1415.
Eriksson et al., *Antimicrobial Agents and Chemotherapy*, vol. 33, No. 10, Oct. 1989, pp. 1729-1734.
Chu, et al., *J. Med. Chem.*, vol. 32, 1989, pp. 612-617.
Camarasa, et al., *J. Med. Chem.*, vol. 28, 1985, pp. 40-46.
International Publication No. WO 89/12062, Dec. 14, 1989.

*Primary Examiner*—John W. Rollins
*Attorney, Agent, or Firm*—Kilpatrick & Cody

[57] ABSTRACT

Compounds of the general formula:

$$R-W-\underset{\underset{WR_1}{|}}{\overset{\overset{W}{\|}}{P}}-W-\underset{\underset{WR_2}{|}}{\overset{\overset{O}{\|}}{P}}-W-\begin{bmatrix}X & Y\\A & B\\Z\\C & D\end{bmatrix}$$

wherein A, B, and C are hydrogen, halogen, or azido; D is hydrogen, halogen, azido, or OH; A and B or C and D can be replaced with a double bond; R is an aldohexose, aldohexosamine, or N-acetyl aldohexosamine, $R_1$ and $R_2$ are hydrogen or alkyl groups of from $C_1$ to $C_{10}$; W is oxygen or sulfur; X is oxygen, sulfur, or $CH_2$; Y is a purine or pyrimidine base, and Z is carbon, sulfur, or oxygen. Y can be any purine or pyrimidine base, natural or synthetic, which combines with a sugar to form a biologically active nucleoside. In combination with an appropriate pharmaceutical carrier, the compositions have enhanced activity or increased intracellular absorbment over the parent nucleoside as a function of the 5'-O-diphosphosugar. Another embodiment of the present invention is the enhancement of biologically active nucleosides into cells by preparing and administering the 5'-O-diphosphohexose, 5'-diphospho-N-acetylhexosamine or 5'-diphosphohexosamine derivative of the nucleoside. In the preferred embodiment for therapeutic use, the compounds are provided in a pharmaceutical carrier in an amount sufficient to exhibit as known *in vitro* or *in vivo* biological activity.

13 Claims, 3 Drawing Sheets proceed to FIGURE 2 continued

R = R$^1$
R = R$^2$
R = R$^3$
R = R$^4$ 1. a = NCCH$_2$CH$_2$OPO$_3$(Py)$_2$
   b = DCC, Pyridine
2. Aq KOH, 100°C 15 Minutes
3. a = morpholine, tert butanol H$_2$O
   b = DCC
4. a = R$^1$, R$^2$ or R$^3$ as their trioctylamine salt, Pyridine
   b = sodium acetate Py = Pyridine
DDC = Dicyclohexylcarbodiimide

5'-DIPHOSPHOHEXOSE NUCLEOSIDE PHARMACEUTICAL COMPOSITIONS

The U.S. Government has rights in this invention as a result of the financial assistance of a Veteran's Administration Merit Review Award and grants from the National Institute of Health.

This is a Continuation-in-Part of U.S. Ser. No. 104.438, entitled "3'-Azido-2',3'-Dideoxyuridine Antiviral Compositions," filed Oct. 2, 1987, by Chung K. Chu and Raymond F. Schinazi, now U.S. Pat. No. 4,916,122, which is a Continuation-in-Part of U.S. Ser. No. 007,473 entitled "3'-Azido-2',3'-Dideoxypyrimidines and Related Compounds as Antiviral Agents" filed Jan. 28, 1987 by Chung K. Chu and Raymond F. Schinazi now abandoned.

BACKGROUND OF THE INVENTION

The present invention is in the pharmaceutical area, and in particular relates to pharmaceutical compositions containing 5'-diphosphohexose and 5'-diphosphohexosamine derivatives of nucleosides.

Acquired immunodeficiency syndrome ("AIDS") was recognized as early as 1979. The number of cases reported to the Centers for Disease Control (CDC) has increased dramatically each year since then, and in 1982 the CDC declared AIDS a new epidemic. Infection with the AIDS virus is highly variable. Initially, the virus replicates abundantly, with virus present in the central nervous system and the cells of the immune system. This is frequently accompanied by fevers, rashes, flulike symptoms and neurological complaints. These symptoms generally disappear within a few weeks, as the amount of virus in the circulation drops. However, virus is still present in the immune cells, the cells of the nervous system, cells of the intestine and bone marrow cells. The victim typically dies two to ten years after the initial asymptomatic period, following a protracted and painful illness.

Human immunodeficiency virus, a retrovirus, is the etiological agent of AIDS, as well as of a variety of related disorders, such as AIDS Related Complex (ARC). HIV infection begins when a virion or virus-infected cell binds to susceptible cells and fuses with them, injecting the core protein and viral RNA into the cell. The RNA is transcribed to viral DNA. The double stranded DNA migrates to the nucleus and is integrated into the cell's DNA. The viral DNA can remain dormant for an indefinite period of time, or the genes can replicate and be translated into viral proteins. The viral proteins are assembled into new virions that bud from the cell, spreading the disease.

HIV preferentially infects the T4 lymphocytes, immune cells important in helping to suppress infection by other agents, thereby impairing proper functioning of the immune system. As a result of impaired immunity caused by the destruction of helper T-cells by the HIV, the host becomes susceptible to opportunistic infections, various types of cancer such as Kaposi's sarcoma, and other disorders associated with reduced functioning of the immune system.

A variety of approaches have been developed to treat AIDS infections, including inhibiting the binding of the virus to host cells with dextran sulfate or soluble CD4 (a glycoprotein found on the surface of cells of the immune system which the HIV binds to when infecting the cells), administration of anti-idiotypic antibodies (an antibody to the antibody against CD4), blockage of viral protein synthesis by compounds such as phosphorothioate, and inhibition of protein glycosylation by compounds such as 2-deoxy-D-glucose. However, these approaches are still in early experimental phases, and have not been approved for clinical treatment.

AIDS and ARC chemotherapy have been recently reviewed by Schinazi, *Strategies and Targets for Anti-Human Immunodeficiency Virus Type 1 Therapy*, "Aids in Children, Adolescents, and Heterosexual Adults: An Interdisciplinary Approach to Prevention," Elsevier, N.Y. 1988); E. D. Clercq, *J. Med. Chem.* 29, 1561–1569 (1986); H. Mitsuya, S. Broder, *Nature* 325, 773–778 (1987); and R. Yarchoan, et al., "AIDS Therapies" *The Science of AIDS* Scientific American (W. H. Freeman and Co. N.Y. 1989).

A number of nucleosides have been found to have anti-HIV activity, including 3'-azido-3'-deoxythymidine (AZT), 2',3'-dideoxycytidine (DDC), 2',3'-dideoxyadenosine (DDA), 3'-azido-2',3'-dideoxyuridine (AzddU), 2',3'-didehydro-2',3'-dieoxycytidine, 3'-deoxy-2',3'-didehydrothymidine, 3'-azido-5-ethyl-2',3'-dideoxyuridine (AzddEU), 3'-azido-5-methyl-2',3'-dideoxycytidine (AzddMeC), 9-(2,3-Dideoxy-2-halo-$\beta$-D-arabinofuranosyl)-$N^6$-methyladenine (2'-halo-$D_2$MeA), and $N^6$-methyl-D-glycero-2',3'-dideoxyfuranosyladenosine ($D_2$MeA). The present application is a continuation-in-part of applications directed to AzddU.

It is generally accepted that the active form of nucleosides such as AZT, AzddU, AzddMeC, $D_2$MeA, and DDC is the triphosphorylated derivative. Triphosphorylated deoxynucleosides appear to inhibit the replication of HIV by limiting the production of viral DNA by at least two mechanisms: competitive inhibition of reverse transcriptase and chain termination of viral DNA due to the missing 3'-hydroxyl group.

The therapeutic effectiveness of all of the known active nucleosides depends on how easily the nucleoside can enter cells and undergo phosphorylation by cellular enzymes. The efficiency of this process varies considerably among nucleosides, and can severely limit the usefulness of the compounds. For example, nucleoside triphosphates without modification, are not useful clinically, since they cannot pass through the cell membrane, even though the triphosphate may have greater antiviral activity.

Nucleosides are also converted by intracellular enzymes into less active metabolites. If the conversion rate to less active compounds is faster than the rate of triphosphorylation of the nucleoside, the pharmaceutical effectiveness of the nucleoside is diminished. For example, it is known that DDA in the triphosphate form is a potent HIV inhibitor in vitro, but in vivo the enzyme adenosine deaminase rapidly converts DDA to the less active DDI (2',3'-dideoxyinosine) before DDA can be phosphorylated. DDI-5'-monophosphate must then be converted to DDA-5'-monophosphate by cellular enzymes to restore the activity of the compound.

The therapeutic effectiveness of a drug is the determining factor in the dosage required for therapy. Nucleosides that pass through the cell membrane with difficulty or which are metabolized into less active or inactive forms in the cell must be administered in higher dosages. Unfortunately, most nucleosides are toxic to healthy uninfected cells at high dosage levels.

AZT has been studied extensively in humans for treatment of HIV infections. However, bone marrow toxicity and other side effects limit its long term usefulness. For example, Richman, et al., have shown that because of AZT-associated hematological abnormalities, twenty-one percent of patients undergoing AZT therapy required multiple blood transfusions during the six month treatment period. Bone marrow depression may be due to the accumulation of phosphorylated AZT within cells, which may result in a substantial depression of thymidine 5'-triphosphate pools. Another drawback of AZT is its short half life in humans (about 1.1 hour) and its elimination in urine as 3'-azido-3'-deoxy-5'-glucuronylthymidine, a metabolite with no substantial antiviral activity.

Many nucleoside derivatives have been developed that have anticancer, anti-bacterial, and anti-fungal activity. Effective therapy with these nucleosides, as with the anti-HIV nucleosides, is significantly affected by the ability of the nucleoside to pass through the cell membrane and diffuse to the active site before the compound is converted to an inactive form or eliminated.

Nucleoside diphosphate sugars are used in vivo for the synthesis of oligosaccharides, polysaccharides, glycolipids, glycoproteins, and components of bacterial cell membranes. Certain nucleoside derivatives have been found to block the glycosylation of proteins. However, most, if not all, known nucleoside glycosylation inhibitors show little selectivity and have low activity against viral infections.

Camarasa, et al., *J. Med. Chem.*, 28, 40 (1985) reported that uridine 5'-diphosphate glucose analogues, 5'-O-[[[[(2",3",4",6"-tetra-O-benzyl- and 2",3",4",6"-tetra-O-benzoyl-α-D-glucopyranosyl)oxy]carbonyl]amino]sulfonyl]-2',3'-isopropylideneuridine (P-536), a UDP-glucose analog, and the corresponding deisopropylidenated derivatives, show in vitro antiviral activity against herpes simplex virus type 1. Alarcon, et al., in *Antimicrobial Agents and Chemotherapy* 1257, (1988) reported that P-536 has broad antiviral activity, including activity against adenovirus type 5, vaccinia virus, and poliovirus type 1. The compound was demonstrated to inhibit protein glycosylation if added at a time when late viral proteins were being synthesized, and to inhibit the synthesis of nucleic acids and phosphorylation of nucleosides. Alcina, et al., *Antimicrobial Agents and Chemotherapy*, 1412 (1988), later demonstrated that the same compound has activity against the flagellated protozoan *Trypanosoma cruzi*.

In light of the state of the art, it is clear that there is a strong need for biologically active nucleoside derivatives that can pass through a cell membrane and reach the active site prior to conversion to inactive metabolites or elimination.

It is therefore an object of the present invention to provide nucleoside derivatives that have enhanced antiviral, antibacterial, antifungal or anticancer activity.

It is a further object of the present invention to provide nucleoside derivatives that can easily pass through a cell membrane in the proper chemical form to perform a desired biological function, or a chemical form.

It is a still further object of the present invention to provide a method to enhance the cellular levels of nucleosides.

SUMMARY OF THE INVENTION

Compounds of the general formula:

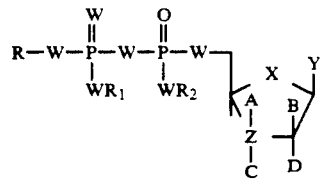

wherein A, B, and C are hydrogen, halogen, or azido; D is hydrogen, halogen, azido, or OH; A and B or C and D can be replaced with a double bond; R is an aldohexose, aldohexosamine, or N-acetyl aldohexosamine; $R_1$ and $R_2$ are hydrogen or alkyl groups of from $C_1$ to $C_{10}$, W is oxygen or sulfur; X is oxygen, sulfur or $CH_2$; Y is a purine or pyrimidine base, Z is carbon, sulfur, or oxygen and wherein when Z is sulfur or oxygen, A and B are not present.

In the preferred embodiment, A, B, and C are hydrogen, halogen, or azido; D is hydrogen, halogen, azido, or OH; A and B or C and D can be replaced with a double bond; R is an aldohexose, aldohexosamine, or N-acetyl aldohexosamine, R1 and R2 are hydrogen; W is O; X is O; Y is a purine or pyrimidine base, and Z is C.

In combination with an appropriate pharmaceutical carrier, the compositions have enhanced activity as a function of the diphosphate group in combination with the sugar.

Y can be any purine or pyrimidine base, natural or synthetic, which combines with a sugar to form a biologically active nucleoside.

A preferred method for enhancing the cellular levels of biologically active nucleosides is to prepare and administer the 5'-diphosphohexose, 5'-diphospho-N-acetylhexosamine or 5'-diphosphohexosamine derivative of the nucleoside.

Methods for prevention or treatment of viral and other diseases, especially AIDS and ARC, are also disclosed, which involve administering an effective dose of a composition containing the 5'-diphosphohexose nucleoside to a patient. Administration of the composition can be accomplished orally, in a controlled release device or in combination with a liposome delivery system, by injection, or other means known to those in the art, alone or in combination with other active agents.

In the preferred method for therapeutic use, the compounds are provided in a pharmaceutical carrier in an amount sufficient to exhibit in vivo biological activity, or in vitro activity in any biological solution containing cells. For example, the composition can be used for inhibition of HIV replication in cell culture, and in the production of pharmaceutical products. The composition is also of value in blood banking procedures.

The biological activity of the compounds, which is enhanced by derivativitization of the diphosphosugar form, is generally known. For example, compounds such as 3'-azido-3'-deoxythymidine (AZT), 2',3'-dideoxycytidine (DDC), 2',3'-dideoxyadenosine (DDA), 3'-azido-2',3'-dideoxyuridine (AzddU), 2',3'-didehydro-2',3'-dideoxycytidine, 3'-deoxy-2',3'-didehydrothymidine, 3'-azido-5-ethyl-2',3'-dideoxyuridine (AzddEU), 3'-azido-5-methyl-2',3'-dideoxycytidine (AzddMeC), 9-(2,3-dideoxy-2-halo-β-D-arabinofuranosyl)-$N^6$-methyladenine (2'-halo-$D_2$MeA), and $N^6$-methyl-D-glycero-2',3'-dideoxyfuranosyladenosine (D₂MeA) are known to possess activity against HIV, which is enhanced by addition of the diphosphate group in combination with the hexose or hexose derivative. 9-β-D-Arabino-furanosyl-2-fluoroadenine is an anticancer agent. 2'-Fluoro-5-ethyl-arabino-furanosyluridine is an antihepatitis and antiherpes agent. Many nucleosides, including some of those listed above, have antibacterial and antiparasitic activity.

DETAILED DESCRIPTION OF THE INVENTION

Figure 1:
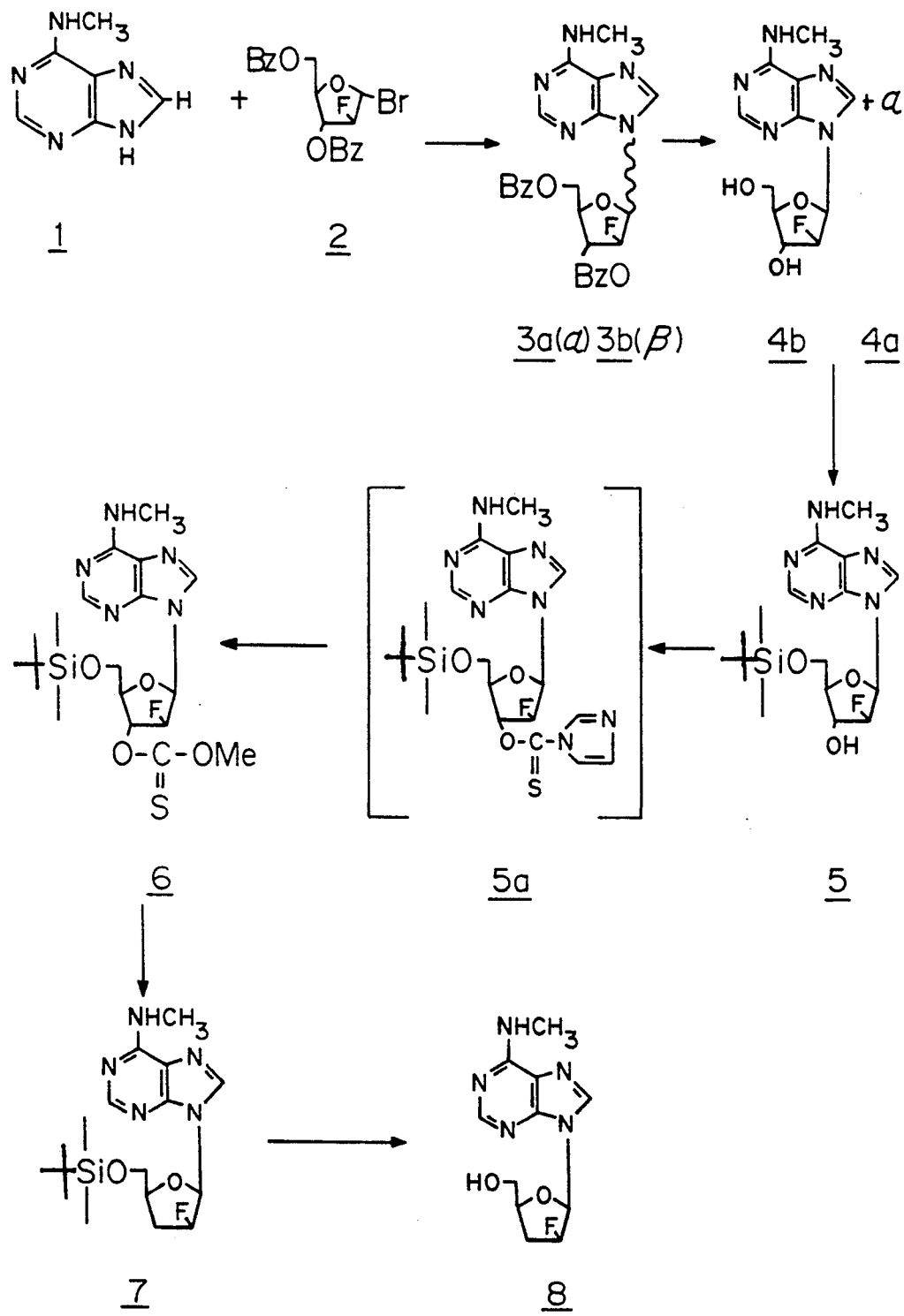
FIG. 1 is an illustration of the method of synthesis of 9-(2,3-dideoxy-2-halo-β-D-arabinofuranosyl)-N⁶-methyladenine (2'-halo-D₂MeA).

Compounds of the general formula:

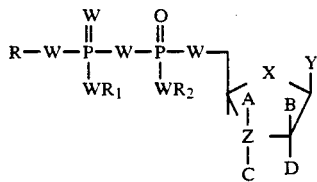

wherein A, B, and C are hydrogen, halogen, or azido; D is hydrogen, halogen, azido, or OH; A and B or C and D can be replaced with a double bond; R is an aldohexose, aldohexosamine, or N-acetyl aldohexosamine; R₁ and R₂ are hydrogen or alkyl groups of from C₁ to C₁₀, W is oxygen or sulfur; X is oxygen, sulfur or CH₂; Y is a purine or pyrimidine base, Z is carbon, sulfur or oxygen and wherein when Z is sulfur or oxygen, A and B are not present.

In the preferred embodiment, A, B, and C are hydrogen, halogen, or azido; D is hydrogen, halogen, azido, or OH; A and B or C and D can be replaced with a double bond; R is an aldohexose, aldohexosamine, or N-acetyl aldohexosamine, R₁ and R₂ are hydrogen; W is O; X is O; Y is a purine or pyrimidine base, and Z is C; are provided in combination with a pharmaceutical carrier for use in vitro or in vivo as antiviral and anticancer compounds. In the most preferred embodiment, A, B, and D are hydrogen and C is an azido group.

R is an aldohexose, aldohexosamine, or N-acetyl aldohexosamine. An aldohexose is a six carbon sugar with an aldehyde group at the end of the carbon chain, such as glucose, galactose, mannose, and fucose (6-deoxygalactose) or a modified sugar such as 2-deoxyglucose, or a halo, azido, dideoxy, or didehydro derivative of the hexose. An aldohexosamine is an aldohexose in which one of the hydroxyl groups has been replaced with an amine, such as glycosamine, galactosamine, and fucosamine.

Alternatively, a ribose, an erythrose, a six carbon sugar without a terminal aldehyde group or an acid modified sugar, such as ascorbic acid, its imine or esterified derivative, may be substituted for the hexose in the diphosphosugar moiety.

X can be oxygen, sulfur, or methylene. For example, the antiviral compound carbovir is an unphosphorylated nucleoside wherein X is CH₂, Y is guanosine, A and B are replaced by a double bond, and C and D are hydrogens. The biological activity of carbovir may be enhanced by adding the diphosphosugar moiety in the 5' position.

Y can be any purine or pyrimidine base, natural or synthetic, which combines with a sugar to form a biologically active nucleoside, such as adenine, guanine, thymine, cytosine, uracil, or derivatives thereof that have been alkylated, halogenated, haloalkylated, haloalkenylated, or hydroxyalkylated. Further, groups such as cyano, $NO_2$, $CH_2NO_2$, SH, or ST, wherein T is an alkyl group of $C_1$ to $C_6$, can be added to the base. Y can be above the ring (forming a β-nucleoside), or below the ring (forming an α-nucleoside).

Z can be oxygen, sulfur, or carbon. When Z is sulfur or oxygen, cytidine, or a cytidine derivative, is a preferred Y substituent.

Examples of 5'-diphosphosugar compounds include the 5'-diphosphohexose, 5'-diphosphohexosamine, or N-acetyl diphosphohexosamine derivatives of 3'-fluoro-3'-deoxythymidine (FLT or FDT), 3'-fluoro-2',3'-dideoxyuridine (FDU), 2',3'-didehydro-3'-deoxythymidine (D4T), 2',3'-dideoxyinosine (DDI), 5-E-(2-bromovinyl)-2'-deoxyuridine (BVDU) and its arabinosyl analogue (BV-ara-U), 3'-azido-3'-deoxythymidine (AZT), 2',3'-dideoxycytidine (DDC), 2',3'-dideoxyadenosine (DDA), 3'-azido-2',3'-dideoxyuridine (AzddU), 2',3'-didehydrocytidine, 3'-deoxy-2',3'-didehydrothymidine, 3'-azido-5-ethyl-2',3'-dideoxyuridine (AzddEU), 3'-azido-5-methyl-2',3'-dideoxycytidine (AzddMeC), 9-(2,3-Dideoxy-2-halo-β-D-arabinofuranosyl)-N⁶-methyladenine (2'-halo-D₂MeA), N⁶-methyl-D-glycero-2',3'-dideoxyfuranosyladenosine (D₂MeA), 9-β-D-arabino-furanosyl-2-fluoroadenine, and 2'-fluoro-5-ethyl-arabino-furanosyluridine.

It has now been discovered that the compounds are absorbed by cells and that the biological activity of the 5'-diphosphohexose nucleosides and 5'-diphosphohexosamine nucleosides and their derivatives appears to be enhanced over that of the nucleoside in the absence of the diphosphohexose group. Another advantage of the derivatized nucleoside is that, after entry into cells, the 5'-diphosphohexose nucleosides do not require the initial phosphorylation by viral or cellular kinases as is necessary for activation of non-phosphorylated nucleosides. For example, it is known that AzddU is converted by cellular kinases to AzddU-5'-monophosphate. However, the diphosphosugar analogues of AzddU do not need to be converted initially to the 5'-monophosphate. After uptake by the cells, they can be converted directly to the active antiviral compound, AzddU-5'-triphosphate. Alternatively, the diphosphosugar nucleoside can be cleaved intracellularly by phosphodiesterases to form a monophosphonucleoside, which can then be converted to the virally active 5'-triphosphate nucleoside, by-passing the first phosphorylation step.

AzddU-5'-diphosphoglucose and diphospho-N-acetylglucosamine have been discovered to be metabolites of AzddU, found in large amounts in primary cells (e.g., human peripheral blood mononuclear cells), and in significantly lower levels in continuous cell lines (e.g., CEM-CCRF, a T-lymphoblastoid cell line obtained from the American Type Culture Collection, Rockville, Md.) 5'-Diphosphohexose nucleosides, however, are not found among the metabolic products of AZT. The production of Azddu-5'-diphosphoglucose and diphospho-N-acetylglucosamine derivatives may explain the low levels of AzddU-triphosphate found in cells, especially bone marrow, and the very low toxicity of AzddU. The AzddU metabolites are believed to be the first examples of 2'-deoxyuridine diphosphatehexose compounds.

The present invention is further described with reference to the following non-limiting examples.

EXAMPLE 1

Synthesis of 5'-Diphosphohexose Nucleosides

5'-Diphosphohexose and 5'-diphosphohexosamine derivatives of nucleosides can be prepared synthetically or enzymatically. In both routes, the first step involves the preparation of the nucleoside. In the second step, the diphosphohexose, hexosamine, or N-acetylhexosamine is added to the nucleoside.

A. Synthesis of Nonphosphorylated Nucleosides

Nonphosphorylated nucleosides can be prepared by methods known to those of skill in the art such as by condensing a sugar molecule with a nitrogenous base (see, for example, Dyatkina, N. B., *Soviet J. Biorg. Chem.* 128 563 (1986); U.S. Pat. No. 4,230,689; Fleet, Son and Drome, *Tetrahedron* 44 (2), 625 (1988); Hafele and Jager, *Liebigs Ann. Chem.* 85 (1987); Baker, Joseph and Schaub, *J. Am. Chem. Soc.* 5905 (1955); Baker, Schaub and Williams, *J. Am. Chem. Soc.* 7 (1955)); or derivatizing a preformed nucleoside (see, for example, Lin, T. S. et al., *J. Med. Chem.*, 26, 544 (1983); Colla, et al. *Eur. J. Med. Chem. -Chim. Ther.* 20(4), 295 (1985); Herdewijn, et al., *J. Med. Chem.* 30, 1270 (1987); Chem Abstract 101:192378c (1984); Horowitz, et al., *J. Am. Chem. Soc.* 86, 1896 (1964); Horowitz, et al., *J. Org. Chem.* 29, 2076 (1984); Herdewijn, et al., *J. Med. Chem.* 30, 1270 (1987); Lin, et al., *Biochem. Pharmacol.* 36, 2713 (1987)).

Nucleosides with sulfur or carbon in the sugar moiety can be synthesized according to the methods of Y. F. Shealy, C. A. O'Dell, *J. of Heterocyclic Chem.*, 13, 1015 (1976); R. Vince, S. Daluga, *J. Med. Chem.*, 120(4), 612 (1977); and C. K. Chu, U. Reichman, V. A. Watanabe, J. J. Fox, *J. Med. Chem.*, 21, 96 (1978).

The following example describes how to prepared 3'-azido-2',3'-dideoxyuridine (AzddU), and 9-(2,3-dideoxy-2-halo-β-D-arabinofuranosyl)-N$^6$-methyladenine (2'-halo-D$_2$MeA), as illustrated in FIG. 1.

3'-Azido-2',3'-Dideoxyuridine (AzddU)

AzzdU is a known compound. For the synthesis of this compound, see, for example, Lin, et al., *J. Med. Chem.* 26, 1691-1696 (1983), and Lin and Mancini, *J. Med. Chem.* 26, 544-548, Colla, et al., *Eur. J. Med. Chem. -Chim. Ther.* 295-301 (1985). The following is a synthetic scheme for the preparation of AzzdU starting from 2'-deoxyuridine.

5'-O-Trityl-2'-Deoxyuridine

A solution of (50 g, 0.22 mole) of 2'-deoxyuridine and 62 g (0.22 mole) of trityl chloride in 350 ml of dry pyridine was placed in a preheated (100° C.) flask and stirred at 100° C. under an air condenser for two hours. The reaction mixture was cooled to room temperature and slowly poured into 4 L of vigorously stirred ice-water. The solid obtained was filtered, washed with water until free from pyridine, and dissolved in chloroform and dried (Na$_2$SO$_4$ or MgSO$_4$). Filtration and evaporation of chloroform yielded the 5'-O-trityl-2'-deoxyuridine product as an syrup (96 g, 93%), which was used for the next reaction without further purification.

3'-O-Mesyl-5'-Trityl-2'-Deoxyuridine

Mesyl chloride (70 ml, 98%, sp. gr. 1480) was added dropwise to an ice cooled solution of 5'-O-trityl-2'-deoxyuridine (96 g, 0.2 mol) in 350 ml of dry pyridine. The mixture was stirred in an ice-water bath for 3 hours and poured slowly into vigorously stirred ice-water. The solid precipitated was filtered, washed with water and dried (101 g, 94%).

2,3'-Anhydro-5'-O-Trityl-2'-Deoxyuridine

3'-O-Mesyl-5'-O-trityl-2'-deoxyuridine (101 g, 0.19 mol) was suspended in 350 ml ethanol (95%) and the mixture was heated to reflux. To the refluxing mixture was added dropwise 125 ml of an aqueous solution of sodium hydroxide (2N). The reaction mixture was concentrated under vacuum. The syrupy residue was purified by flash vacuum chromatography over a silica gel column eluting sequentially with chloroform, chloroform-methanol (50:1) and finally with chloroform-methanol (30:1). Evaporation of the pure fractions yielded 72 g (88%) of white powder, 2,3'-anhydro-5'-O-trityl-2'-deoxyuridine.

3'-Azido-5'-O-Trityl-2',3'-Dideoxyuridine

A mixture of 2',3'-anhydro-5'-O-trityl-2'-deoxyuridine (72 g, 0.165 mol) and 50 g of lithium azide in 250 ml of dry dimethylformamide was heated at 110°-120° C. for 12 hours. The reaction mixture was cooled and slowly poured into 4 L of ice-water. The solid obtained was filtered, washed with water, and dissolved in chloroform and dried (MgSO$_4$). Filtration and evaporation of chloroform yielded 63 g (80%) of the product as a syrup.

3'-Azido-2',3'-Dideoxyuridine (AzddU)

A mixture of 3'-azido-5'-O-trityl-2',3'-dideoxyuridine (63 g, 0.132 mol) and 300 ml of acetic acid (80%) was heated at 95°-100° C. for two hours. The reaction mixture was cooled in an ice-bath and the solid separated was filtered off. The filtrate was evaporated to dryness. The residue was dissolved in a methanol-chloroform mixture and concentrated to a syrup. The residue was purified by flash vacuum chromatography over a silica gel column eluting sequentially with chloroform-methanol (70:1), chloroform-methanol (50:1) and finally chloroform-methanol (30:1), to yield 23 g (70%) of 3'-azido-2',3'-dideoxyuridine.

9-(2,3-Dideoxy-2-Halo-β-D-Arabinofuranosyl)-N$^6$-Methyladenine (2'-Halo-D$_2$MeA)

9-(2,3-Dideoxy-2-halo-β-D-arabinofuranosyl)-N$^6$-methyladenine (2'-halo-D$_2$MeA) can be synthesized from N$^6$-methyladenine by the following scheme. First, the sodium salt of N$^6$-methyladenine is produced in situ with NaH in anhydrous dimethyl formamide. The sodium salt of N$^6$-methyladenine is then reacted with 3,5-dibenzoyl-1-bromo-2-deoxy-2-halo-α-D-arabinofuranose, which can be produced by the method of C. H. Tann et al., *J. Org. Chem.* 50, 36-44 (1985). In the method of Tann, 1,3,5-tri-O-benzoyl, 2-imidazolylsulfonylfuranose is fluorinated with KHF$_2$ to yield 2-deoxy-2-fluoro-1,3,5-O-benzoyl-α-D-arabinofuranose, which is reacted with HBr in acetic acid to produce compound 2 (FIG. 1). Alternatively, the halogen can be added to the furanose by reaction of the 2-OH moiety with triphenylphosphine followed by $CCl_4$, $CBr_4$, or $CI_4$, at a reaction temperature of between approximately 23° C. and 60° C.

A halogen can also be added to the 2-position of the furanose ring by first reacting the 2-OH moiety with mesyl sulfonyl chloride in pyridine to form the mesylsulfonyl ester. The ester is isolated and then refluxed with KCl, NaBr, or NaI in an organic solvent such as dimethylformamide (DMF) or dimethylsulfoxide (DMSO) to form the halodeoxy sugar.

The reaction of compound 2 with the sodium salt of $N^6$-methyladenine produces a mixture of α and β anomers, 3a and 3b.

The mixture of 3a and 3b can be debenzoylated by treatment with methanol saturated with ammonia to produce 4a and 4b. The α-anomer 4a is then separated from the β-anomer 4b with flash column chromatography.

The 5'-hydroxyl group of 4b is then reacted with t-butyl-dimethylsilychloride in DMF to form the corresponding t-butyldimethylsilyl protected nucleoside 5. The 5'-protected nucleoside 5 can be treated with excess N,N-thiocarbonyldimidazole in DMF at 80° C. for 10 hours to give intermediate imidazolides 5a, which upon reaction with methanol at 50° C. for 2 hours, yields crystalline methylthionocarbonate 6. Treatment of 6 with tri-n-butyltinhydride and triethylborane in anhydrous tetrahydrofuran under argon produces 7 in excellent yield. The final product 8 is produced by desilylation of 7 with tetrabutylammonium flouride (TBAF) in THF at room temperature.

B. Chemical Synthesis of 5'-O-Diphosphohexose Nucleosides

5'-Diphosphohexose, 5'-diphosphohexosamine and 5'-diphospho-N-acetylhexosamine nucleosides can be prepared from the corresponding nucleoside 5'-monophosphates by reaction with dicyclohexylcarbodiimide and morpholine to form a 5'-phosphomorpholidate-4-morpholino-N,N-dicyclohexyl carboxamidium salt, which is then reacted with an α-D-sugar-1-phosphate-tri-n-octyl amine salt to form the desired product. See generally: Kochetkov, N. K. et al., *Tetrahedron* 19, 1207–1218 (1963); Tener, G. M., *J. Amer. Chem. Soc.* 83, 154 (1961); Michelson, A. M. and Todd, A., *J. Amer. Chem. Soc.* 3459 (1956); Roseman, S., Distler, J. J., Moffat, J. G. and Khorana, H. G., *J. Amer. Chem. Soc.* 83, 659 (1961); Weekbecker, G. and Keppler, D., *Analyt. Biochem.* 132, 405 (1957); and Ludwig, J. and Eckstein, F., *J. Org. Chem.* 54, 631 (1989). 5'-Diphosphohexosamines can be acetylated according to the procedure of Weekbecker, G. and Keppler, D., *Analyt. Biochem.* 132, 405 (1957).

Figure 2:
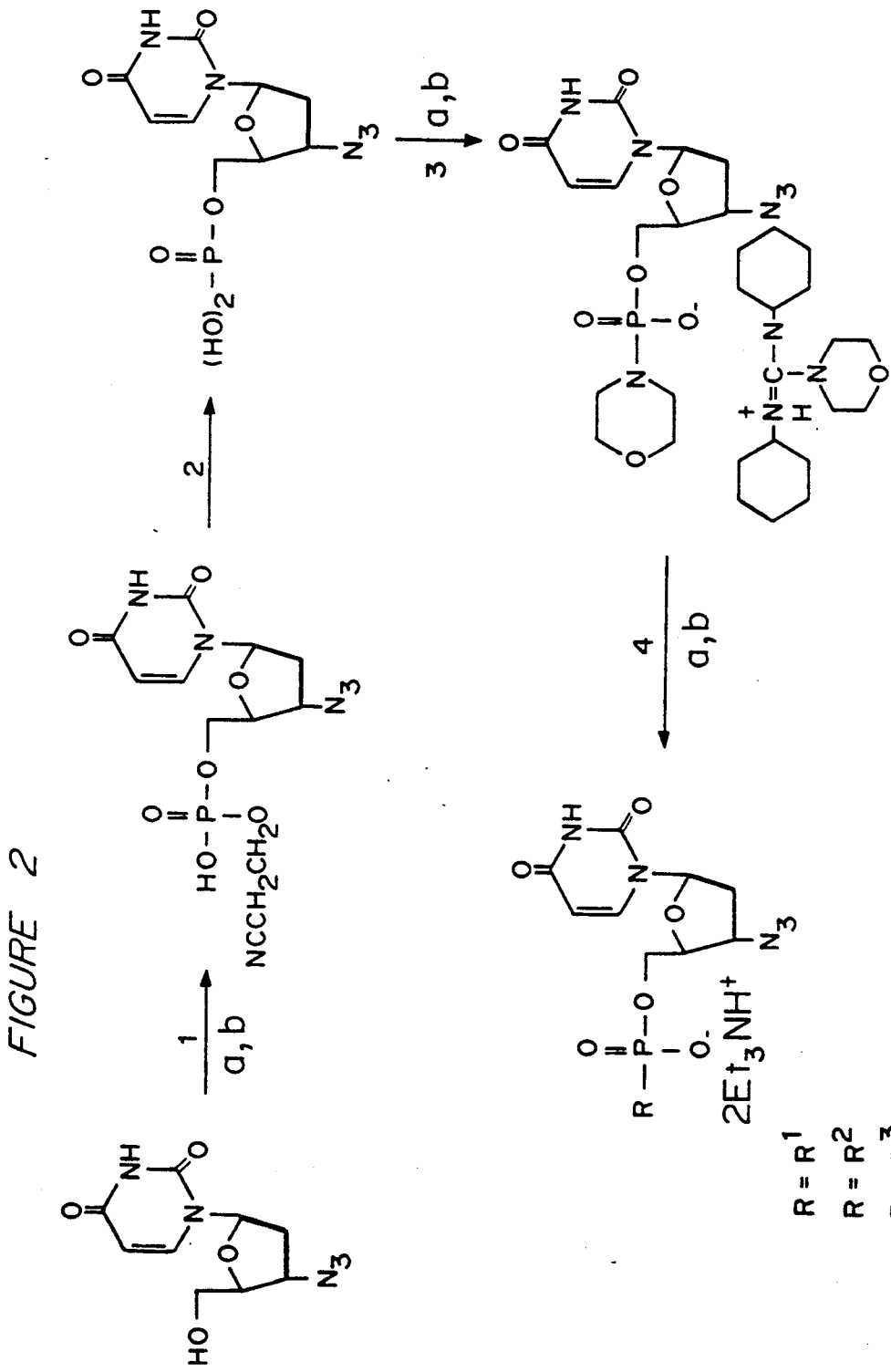
FIG. 2 is an illustration of the method of synthesis of 3'-azido-5'-O-diphosphoglucose-2',3'-dideoxyuridine, 3'-azido-5'-O-diphosphoglucosamine-2',3'-dideoxyuridine, and 3'-azido-5'-O-diphospho-N-acetylglucosamine-2',3'-dideoxyuridine.
Figure 2:
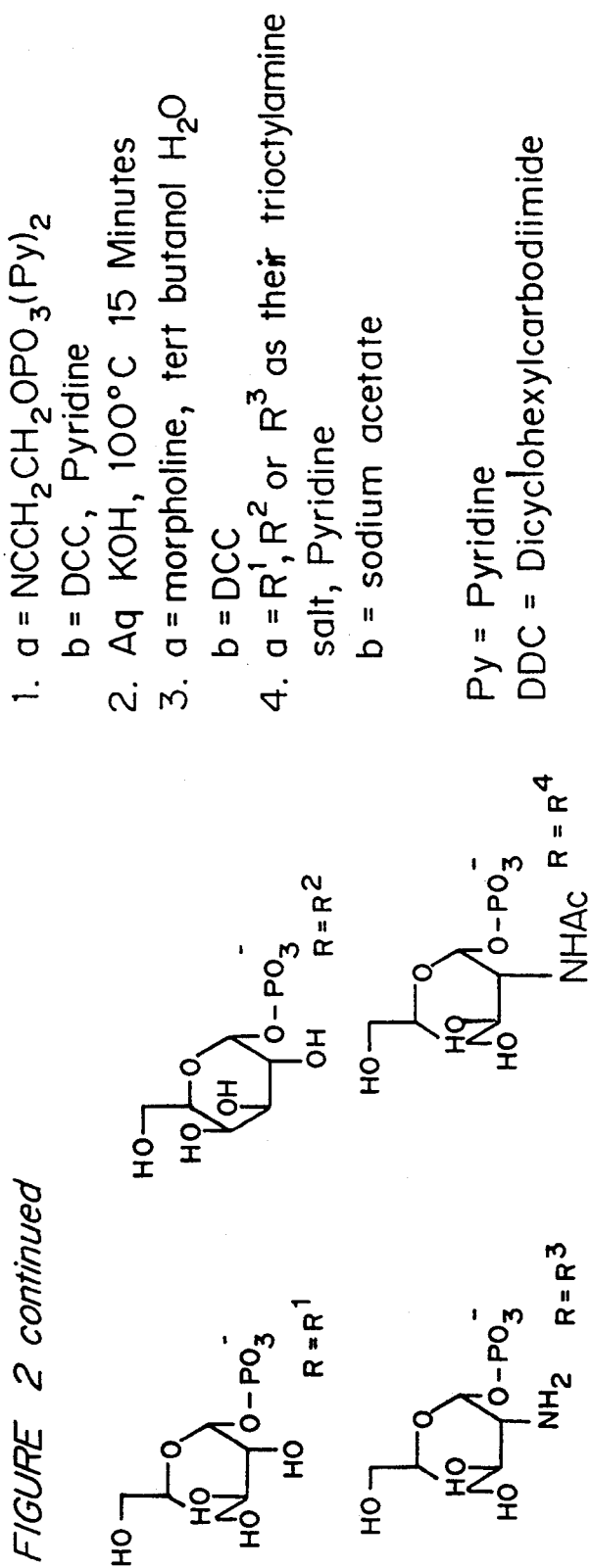

The following is a detailed procedure for the preparation of 3'-azido-2',3'-dideoxyuridine-5'-diphosphohexose and 3'-azido-2',3'-dideoxyuridine-5'-diphosphohexosamine and the corresponding N-acetyl hexosamines, as illustrated in FIG. 2.

3'-Azido-2',3'-Dideoxyuridine-5'-Monophosphate

A freshly prepared pyridinium salt of 2-cyanoethyl-phosphate (8.05 g, 23.64 mmol) was added to a solution of 3'-azido-2',3'-dideoxyuridine (2.50 g, 9.7 mmol) in dry pyridine (50 ml) and evaporated to dryness at 30° C. The concentrated residue was dissolved in pyridine (50 ml) and the solution again evaporated to dryness. The process was repeated twice and then the residue obtained was dissolved in dry pyridine (50 ml). Dicyclohexylcarbodiimide (8.08 g, 39.1 mmol) was added to the solution. The reaction mixture was stirred for 48 hours at room temperature. Water (10 ml) was added and the solution was then filtered to remove dicyclohexylurea. The clear solution was evaporated to dryness. The residue obtained was then dissolved in 1N KOH (250 ml) and heated for 15 minutes at 100° C. The cold solution was passed through a column of acidic Dowex 50 (H+), the effluent brought to pH 9 and passed through a column of Dowex (1×4 Cl−). A linear gradient elution of 0.015N HCl to 0.15N HCl resulted in 3'-azido-2',3'-dideoxyuridine-5'-monophosphate with a 73% yield.

3'-Azido-2',3'-Dideoxyuridine-5'-Phosphomorpholidate

A solution of dicyclohexylcarbodiimide (2.86 g, 13.87 mmol) in t-butanol (50 ml) was added to a solution of 3'-azido-2',3'-dideoxyuridine-5'-monophosphate (1.20 g, 3.6 mmol) in $H_2O$ (36 ml) and containing morpholine (1.2 ml, 13.7 mmol) in 36 ml of t-butanol. The reaction mixture was refluxed for 1 hour and then stirring of the mixture was continued for another 18 hours. The dicyclohexylurea was then filtered off, and the solution was extracted with diethyl ether (150 ml). The aqueous phase was evaporated to dryness. The obtained residue was dissolved in methanol and then precipitated with ether to give 3'-azido-2',3'-dideoxyuridine-5'-phosphomorpholidate-4-morpholino-N,N-dicyclohexylcarboxamidinium salt (1.58 g, 68%).

3'-Azido-2',3'-Dideoxyuridine-5'-Diphosphoglucose,

3'-Azido-2',3'-Dideoxyuridine-5'-Diphosphoglucosamine and

3'-Azido-2',3'-Dideoxyuridine-5'-Diphospho-N-Acetylglucosamine

A freshly prepared α-D-sugar-1-phosphate-tri-n-octyl amine salt (2 to 3 equivalents) was added to a solution of 3'-azido-2',3'-dideoxyuridine-5'-phosphomorpholidate-4-morpholino-N,N-dicyclohexylcarbonamidinium salt in dry pyridine and evaporated to dryness. The process of dissolution in fresh dry pyridine and evaporation was repeated twice. Pyridine (dry) was added to the residue and then the solution obtained was stirred at room temperature for 42 hours. The reaction mixture was then left for 4 hours at 60° C., and the progress of reaction followed by thin layer chromatography [ethanol:$NH_4OH$:water (10:10:1)]. The solvent was then evaporated, and then water containing sodium acetate (20% more than the amount of corresponding salt) was added to the mixture. The solution was extracted with ether. The combined aqueous layers were evaporated. The residue obtained was chromatographed on DEAE-sephadex and eluted with increasing concentrations of triethyl ammonium acetate pH 4.0 (linear gradient of 0.1M buffer-1.0M buffer) to yield either 3'-azido-2',3'-dideoxyuridine-5'-diphosphoglucose, -galactose, or -glucosamine.

3'-Azido-2',3'-Dideoxyuridine-5'-Diphospho-N-Acetylglucosamine

The solution of 3'-azido-2',3'-dideoxyuridine-5'-diphosphoglucosamine (0.080 mmol) in $H_2O$ (1.0 ml) was treated with acetic anhydride (5 equivalent) (0.0408 g, 0.40 mmol) in $CH_3OH$ (0.5 ml) containing $H_2O$ (20%) at 0° C. The resulting mixture was stirred for another 18 hours at 0° C. The solution was concentrated and the residue obtained was then chromatographed on DEAE-sephadex as described above to yield 3'-azido-2',3'-dideoxyuridine-5'-diphosphate-N-acetylglucosamine (53%).

C. Enzymatic Synthesis of 5'-O-Diphosphohexose Nucleosides

5'-O-Diphosphoglucose nucleosides can be prepared from the reaction of the corresponding triphosphorylated nucleosides with glucose1-phosphate in the presence of inorganic pyrophosphatase and bacterial diphosphoglucose-pyrophosphorylase. For example, if a 5'-O-diphosphoglucose uridine nuceloside is desired, the enzyme uridine diphosphoglucose-pyrophosphorylase is used. If 5'-O-diphosphogalactose uridine is desired, the enzyme uridine diphosphogalactose pyrophosphorylase is substituted for uridine diphosphoglucosepyrophosphorylase. Alternatively, a 5'-O-diphosphogalactose nucleoside can be prepared by epimerization of the glucose molecule of 5'-O-diphosphoglucose uridine nucleoside by the enzyme uridine diphosphoglucose-4-epimerase. These enzymes can be commercially obtained from Sigma Chemical Company. Currently, enzymes are not available for the synthesis of 5'-O-diphospho-N-acetylhexosamine nucleosides or 5'-O-diphosphofucose nucleosides.

5'-O-Triphosphonucleoside can be prepared from the corresponding monophosphates as described by Hoard, et al., *J. Am. Chem. Soc.*, 87(8) 1785–1788 (1965). The monophosphates can be prepared by the method of Imai, *J. Org. Chem.*, 34(6), 1547–1550 (1969), or as described in Section B above.

The following example further illustrate how to prepare the 5'-O-diphosphohexose nucleosides enzymatically.

Synthesis of
3'-Azido-2',3'-Dideoxyuridine-5-O-Diphosphoglucose

To 150 milligrams of AzddU-triphosphate was added 400 milligrams of glucose-1-phosphate, 6 millimole of $MgCl_2$, 0.70 millimole of Tris-HCl pH 7.6, bacterial UDPG-pyrophosphorylase and inorganic pyrophosphatase. After 4 hours at room temperature, the reaction was stopped with perchloric acid (7N). After 30 minutes in ice, samples were centrifuged and the supernatant was neutralized with base. After another 30 minutes in ice, samples were recentrifuged and AzddU-5'-diphosphoglucose was purified by column chromatography.

EXAMPLE 2

Anti-HIV Activity in Human Peripheral Blood Mononuclear Cells

Assay

A. Three-day-old phytohemagglutinin-stimulated PBM cells ($10^6$ cells/ml) from hepatitis B and HIV-1 seronegative healthy donors were infected with HIV-1 (strain LAV) at a concentration of about 100 times the 50% tissue culture infectious dose ($TICD_{50}$) per ml and cultured in the presence and absence of various concentrations of antiviral compounds.

B. Approximately 45 minutes after infection, medium, with the compound to be tested (2 times the final concentration in medium) or without compound, was added to the flasks (5 ml; final volume 10 ml). AZT was used as a positive control.

C. The cells were exposed to HIV (about $2 \times 10^5$ dpm/ml, as determined by reverse transcriptase assay) and then placed in a $CO_2$ incubator. HIV-1 (strain LAV) was obtained from the Center for Disease Control, Atlanta, Ga. The methods used for culturing the PBM cells, harvesting the virus and determining the reverse transcriptase activity were those described by McDougal et al. (*J. Immun. Meth.* 76, 171–183, 1985) and Spira et al. (*J. Clin. Meth.* 25, 97–99, 1987), except that fungizone was not included in the medium (see Schinazi, et al., *Antimicrob. Agents Chemother.* 32, 1784–1787 (1988)). The reverse transcriptase activity in the virus-infected control was about $2 \times 10^5$ dpm per ml. Blank and uninfected cell control values were about 300 and 1,000 dpm, respectively.

D. On day 6, the cells and media were transferred to a 15 ml tube and centrifuged at about 900 g for 10 minutes. Five ml of supernatant were removed and the virus concentrated by centrifugation at 40,000 rpm for 30 minutes (Beckman 70.1 Ti rotor). The solubilized virus pellet was processed for determination of the levels of reverse transcriptase. Results are expressed in dpm/ml of sampled supernatant.

Results

The median effective ($EC_{50}$) concentrations for AzddU-5'-diphosphohexoses, were determined by the median effect method (*Antimicrob. Agents Chemother.* 30: 491–498, 1986). Briefly, in the median effect method, the percent inhibition of virus, as determined from measurements of reverse transcriptase, is plotted versus the micromolar concentration of compound. The $EC_{50}$ is the concentration of compound at which there is a 50% inhibition of viral replication.

The median effective concentration of AzddU-5'-diphosphoglucose against HIV is 0.03 micromolar, which is approximately 10 times lower than the value for the parent drug, AzddU, of 0.2 micromolar.

EXAMPLE 3

Determination of Toxicity of
3'-Azido-2,3'-Dideoxyuridine-5'-Diphosphohexose in Peripheral Blood Mononuclear Cells Assay The toxicity of compounds, was determined in mitogen-stimulated PBM cells ($3.8 \times 10^5$ cells/ml) cultured in the presence and absence of compounds under conditions similar to those used for the antiviral assay described above but without virus. The cells were counted after 6 days using a hemacytometer and the trypan blue exclusion method, as described by Schinazi et al., *Antimicrobial Agents and Chemotherapy*, 22(3), 499 (1982).

Results

The effect of the compounds on the growth of uninfected human PBM cells in culture is used as an indicator of the toxicity of the test compound to the normal viability of cells. The $IC_{50}$ is the concentration of compound which inhibits 50% of normal, uninfected, cell growth. 3'-Azido-2',3'-dideoxyuridine-5'-diphosphoglucose was determined to have an $IC_{50}$ of greater than 100 $\mu$M in cultured PBM cells.

EXAMPLE 4

Preparation of 5'-Diphosphohexose Nucleoside Pharmaceutical Compositions

Derivitization of nucleosides to form 5'-diphosphohexose nucleosides is useful therapeutically both in vitro and in vivo to increase absorption and/or activity of biologically active nucleosides. For example, nucleosides are known which are effective as antiviral or anticancer agents, acting primarily to inhibit viral replication, either as an inhibitor of transcription or translation or by interfering with glycoprotein synthesis and thereby the mechanism by which viruses infect cells and replicate.

Pharmaceutical carriers suitable for administration of the compounds are known to those skilled in the art, depending on the mode of administration. The active materials can be administered by any appropriate route, for example, orally, parenterally, intravenously, intradermally, subcutaneously, or topically, in liquid or solid form. Because of the enhanced biological activity, the effective dosage of the derivatized nucelosides will be less than the effective dosage of the underivatized nuceloside. For example, the effective dosage of 3'-azido-2',3'-dideoxyuridine-5'-diphosphohexose is approximately ten times less than the effective dosage of 3'-azido-2',3'-dideoxyuridine.

The active compound is included in the pharmaceutically acceptable carrier in an amount sufficient to exert a therapeutically useful effect in the absence of serious toxic effects on the patient treated. For example, an "HIV inhibitory amount" is an amount of active ingredient sufficient to exert an HIV inhibitory effect as measured by an assay such as the ones described in Example 2. These preparations should produce a serum concentration of active ingredient of from about 0.2 to 40 $\mu$M. A preferred concentration range is from 0.2 to 20 $\mu$M and most preferably about 1 to 10 $\mu$M. The pharmaceutical compositions should provide a dosage of from 1 to 60 milligrams of compound per kilogram of body weight per day.

The concentration of active compound in the drug composition will depend on absorption, inactivation, and excretion rates of the active compound as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions. The active ingredient may be administered at once, or may be divided into a number of smaller doses to be administered at varying intervals of time.

Some compounds, such as 2',3'-dideoxyadenosine and 2',3'-dideoxy-$N^6$-methyladenosine, and their diphosphohexose derivatives which have anti-HIV activity, are acid labile. If oral administration is desired, the compound must be provided in a composition that protects it from the acidic environment of the stomach. The compound can be orally administered in combination with an antacid formulation. The composition can also be administered in an enteric coating that maintains its integrity in the stomach and releases the active compound in the intestine. A preferred mode of administration of the compounds of this invention is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antibiotics, antifungals, antiinflammatories, or other antivirals, including other nucleoside antiviral or anticancer compounds.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceutical, Inc.

Liposomal suspensions (including liposomes targeted to infected cells with monoclonal antibodies to viral antigens) are also preferred as pharmaceutically acceptable carriers. These may be prepared according to methods known to those skilled in the art, such as the method described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the diphosphohexose nucleoside derivative is then introduced into the container, the container is swirled by hand to free lipid material from the sides of the container and to disperse lipid aggregates, and thereby form the liposomal suspension.

Modifications and variations of the 5'-diphosphosugar compounds, pharamaceutical preparations and methods of use thereof, will be apparent to those of skill in the relevant art from the foregoing detailed description. Such modifications and variations are intended to come with the scope of the following claims.

We claim:

1. A compound of the formula

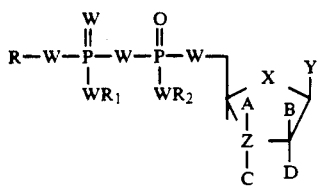

wherein A, B, and C are hydrogen, halogen, or azido; D is hydrogen, halogen, azido, or OH; A and B or C and D can be replaced with a double bond; R is an aldohexose, aldohexosamine, or N-acetyl aldohexosamine; $R_1$ and $R_2$ are hydrogen or alkyl groups from $C_1$ to $C_{10}$, W is oxygen or sulfur; X is oxygen, sulfur or $CH_2$; Y is a purine or pyrimidine base, and Z is carbon, sulfur, or oxygen, and wherein when Z is sulfur or oxygen, A and C are not present.

2. The compound of claim 1 wherein $R_1$ and $R_2$ are hydrogen; W is oxygen; X is oxygen; Y is a purine or pyrimidine base; and Z is oxygen.

3. The compound of claim 1 selected from the group consisting of the 5'-diphosphohexose, 5'-diphosphohexosamine, or N-acetyl diphosphohexosamine derivatives of 3'-fluoro-3'-deoxythymidine, 3'-fluoro-2',3'-dideoxyuridine, 2',3'-didehydro-3'-deoxythymidine, 2',3'-dideoxyinosine, 5-E-(2-bromovinyl)-2'-deoxyuridine and its arabinosyl analogue (BV-ara-U), 3'-azido-3'-deoxythymidine, 2',3'-dideoxycytidine, 2',3'-dideoxyadenosine, 3'-azido-2',3'-dideoxyuridine, 2',3'-didehydro-2',3'-dideoxycytidine, 3'-deoxy-2',3'-didehydrothymidine, 3'-azido-5-ethyl-2',3'-dideoxyuridine, 3'-azido-5-methyl-2',3'-dideoxycytidine, 9-(2,3-Dideoxy-2-halo-$\beta$-D-arabinofuranosyl)-$N^6$-methyladenine, $N^6$-methyl-D-glycero-2',3'-dideoxyfuranosyladenosine, 9-$\beta$-D-arabino-furanosyl-2-fluoroadenine, and 2'-fluoro-5-ethyl-arabino-furanosyluridine.

4. The compound of claim 1 wherein Y is selected from the group consisting of natural and synthetic purine and pyrimidine bases which combine with a sugar to form a biologically active nucleoside.

5. The compound of claim 1 wherein the R group is selected from the group consisting of glucose, galactose, mannose, fucose, 2-deoxy-glucose or a halo, azido, dideoxy, or didehydro derivative of hexose.

6. The compound of claim 1 wherein X is oxygen.

7. The compound of claim 1 wherein Y is selected from the group consisting of adenine, guanine, thymine, cytosine, uracil, and alkylated and halogenated derivatives of adenine, guanine, cytosine, and uracil.

8. The compound of claim 1, wherein Z is selected from the group consisting of sulfur and oxygen and Y is selected from the group consisting of cytidine, alkylated cytidine, and halogenated cytidine.

9. The compound of claim 1, wherein X is $CH_2$, Y is guanine, A and B together form a double bond, and C and D are hydrogens.

10. The compound of claim 1, wherein X is O, Y is uridine, A, B, and D are hydrogens, and C is azido.

11. The compound of claim 1, wherein W is O.

12. The compound of claim 1, wherein $R_1$ and $R_2$ are hydrogen, W is oxygen, X is oxygen, Y is a purine or pyrimidine base, and Z is carbon.

13. The compound of claim 1, wherein $R_1$ and $R_2$ are hydrogen, W is oxygen, X is oxygen, Y is a purine or pyrimidine base, and Z is sulfur.

* * * * *